United States Patent [19]

Gajic

[11] Patent Number: 4,872,900

[45] Date of Patent: Oct. 10, 1989

[54] BIOREGULATOR BASED ON PLANT RAW MATERIALS AND METHOD FOR PRODUCING SAME

[75] Inventor: Branco R. Gajic, Bulevar Lenjina 105/7, Novi Beograd, 11070, Yugoslavia

[73] Assignees: Patentverwertungsgesellschaft bürgerlichen Rechts; Götz Dorndorf, both of Frankfurt am Main, Fed. Rep. of Germany; Branco Gajic, Yugoslavia

[21] Appl. No.: 159,991

[22] Filed: Feb. 24, 1988

[30] Foreign Application Priority Data

Feb. 27, 1987 [YU] Yugoslavia .............................. 309/87

[51] Int. Cl.$^4$ ............................................. C05F 11/10
[52] U.S. Cl. ............................................. 71/23; 71/1; 71/11
[58] Field of Search ...................... 71/1, 3, 6, DIG. 1, 71/11, 23, 27

[56] References Cited

PUBLICATIONS

Central Patents Index, Basic Abstracts Journal, Section C, Woche Y/18, No. 31899.

*Primary Examiner*—Ferris H. Lander
*Attorney, Agent, or Firm*—Spencer & Frank

[57] ABSTRACT

A bioregulator based on plant raw materials, which consists of certain components of the plants of the Caryophillaceac family. The developed bioregulator is a plant growth regulator of natural origin that can be used in numerous different ways. Depending on the cultivation in question, the bioregulator is applied either to the seeds or to the leaves of the plants. Due to the fact that the bioregulator is made from plant raw materials it is will not pollute the environment.

8 Claims, No Drawings

BIOREGULATOR BASED ON PLANT RAW MATERIALS AND METHOD FOR PRODUCING SAME

DESCRIPTION

The invention pertains to a bioregulator based on plant raw materials as well as to a production method of same.

For stimulating plant growth and for plant-protection mostly synthetic substances are being used. These have the negative effect that they are an ecological burden. Plant-protecting agents can even be fatal to some species of animal. Even if the used substances are relatively harmless they do reduce the fertility of the soil when used regularly. In certain cases harmful residues may collect in the soil.

SUMMARY OF THE INVENTION:

The invention avoids these drawbacks. The foremost object of this invention is to create a bioregulator, i.e. a plant growth regulator that is completely non-toxic and ecologically harmless on the one hand, but can be applied in numerous ways to plants to stimulate their growth on the other hand.

The obtained bioregulator features the below-mentioned main components if necessary with the usual supplements, such as mineral fertilizers and/or plant-protecting agents,
a. 20 to 30 weight % Herniaria
b. 8 to 14 weight % Buffonia
c. 10 to 16 weight % Spergula
d. 30 to 40 weight % Ortega
e. 5 to 7 weight % Arenaria
f. 6 to 8 weight % Sagina
g. 4 to 6 weight % Holesteum and
h. 0 to 10 weight % other plant components.

Tests have proven that particularly good results can be achieved if the main components are present in the following percentages:
a. 24.3 weight % Hernialia
b. 10.6 weight % Buffonia
c. 12.8 weight % Spergula
d. 34.7 weight % Ortega
e. 5.6 weight % Arenaria
f. 6.5 weight % Sagina
g. 4.3 weight % Holesteum and
h. 1.2 weight % other plant components.

The method for production of the described bioregulator is distinguished by the fact that said main components in the above reference weight percentages are ground separately in a mill to granules with an average diameter of 0.5 to 100 $\mu$m, but preferably 1 to 3 $\mu$m and then mixed together and that the mixture is then—with the addition of a suitable extracting substance, preferably n-Butanol—made into a mass with a plastic consistency which is then dried.

Tt is advisable for the extraction substance to be added gradually to the mixture over a period of about 60 minutes and at a temperature of between 20° C. and 40° C. of the mixture; whilst the extracting substance is being added the mixture should be stirred constantly at 400 to 500 revolutions per minute. After this procedure the mass with a plastic consistency is dried at a temperature of 50° C. until a constant level of moisture is reached. Afterwards degranulation may be carried out and subsequently the packing.

Thus the invented bioregulator is a plant growth regulator of natural origin which can be applied for numerous reasons to a variety of plants. The concept of the bioregulator is the interaction between cultivated and wild plants. Due to its bio-regulatory effect this natural product influences the metabolism—respiration, assimilation and photosynthesis—of plants during their autotrophic and heterotrophic phases of growth. The developed bioregulator stimulates the growth, the development and thus the yield—i.e. the number and size of the fruit—of the plants.

The bioregulator can be applied to the seeds, whereby the mobilisation of the germinating reserves is improved, thus strengthening the seedling and in some cases speeding up growth. The subsequent intensive growth and development of the root system of the plants are of great importance and allow a much more effective absorption of both nutrients and water. The larger root system gives the treated plants an advantage which remains until the plants are harvested. It should be mentioned that all plants can be treated with the bioregulator, i.e. even flowers.

It is also possible to apply the bioregulator to the leaves thus increasing the chlorophyll content of the leaves and making more use of the energy of light. This leads to a positive influence on important quality-decisive substances (proteines, oils, sugar, vitamins) of the plants.

The advantages of treating all kinds of plants with the developed bioregulator lie first and foremost in the stimulation of the germinating energy, in the strong development of root system, in the improved absorption of water and nutrients, in a higher chlorophyll content of the leaves combined with more effective use the sun's energy, in greater resistance to parasites and diseases, in less sensitivity to erratic climatic conditions, in an acceleration of the ripening process and an earlier harvest with a higher yield. At the same time the quality is improved due to, for instance, a higher oil and protein content, a higher vitamin and protein content, an increased dry mass content and a more even colouring and size of the fruit. The bioregulator can be stored easily and safely. Either no or very little fertilizers are necessary when the bioregulator is used. The application of same requires almost no additional labour.

Depending on the plant to be sown the bioregulator is either applied to the seeds and/or to the leaves. Exactly how much and when it is applied is also dependent on the plant in question. On the whole the bioregulator is applied by spraying, whereby it is dissolved in the necessary amount of warm water. In the case of seed application the bioregulator may also be applied in the form of a powder. The application does not require precautionary or protective measures. The bioregulator is harmless for human beings, animals and the environment. It is possible to mix plant-protecting agents with it, but much less of such agents will be required.

As has already been said, the object of developing natural bioregulators is to apply them in order to stimulate the growth and development of the plants and to increase the yield and improve the quality of agricultural products. A secondary positive effect of the use of this natural bioregulator is the fact that it also improves the quality of the soil thus leading to a decrease in the amount of fertilizer needed. Use of the bioregulator inreases the yield and also improves the plant's absorption of mineral fertilzers.

An important secondary effect is the reduction of the required plantprotecting agents. By applying the natural bioregulator to plants the immunological plant characteristics are improved and, additionally, the plants are able to withstand the stress periods better which are caused by the application of protective substances.

The natural bioregulator which is extracted from plant raw materials contains natural, physiologically active groups of compounds (phytohormones, mediators and inhibitors). These compounds are contained in the bioregulator in natural, relatively optimal mutual proportions that take the relationship bioregulator-organism-surroundings into consideration.

DESCRIPTION OF A PREFERRED EMBODIMENT:

The basic materials for the carrying out of the registration procedure are plants which belong to the family Caryophillaceae, namely: Herniaria, Buffonia, Spergula, Ortega, Arenaria, Sagina and Holosteum. The procedure will be carried out successively. The plant raw materials will be ground in the exactly specified weight proportions in the appropriate grinders until the seed granulate reaches the size $D = 1 - 3 \times 10^{-5}$ cm. If necessary, one or other main ingredient can be omitted, whereby however the effectiveness of the bioregulator will be reduced accordingly.

For the successive carrying out of the procedure, the basic substances, divided into weight percentages of 100% of the chosen weight unit per load, will be taken in the following proportions:

| | | |
|---|---|---|
| Herniaria L | 24.3% | |
| Buffonia | 10.6% | |
| Spergula L | 12.8% | |
| Ortega L | 34.7% | |
| Arenaria L | 5.6% | |
| Sagina L | 6.5% | |
| Holosteum L | 4.3% | |
| other | 1.2% | 100% |

The plants used will be ground individually. The procedure will be continued in a mixing reactor. The weighed amounts will be added individually unter constant stirring either by hand or automatically, with the appropriate effect of the polar extract substance—n-Butanol. A mixing reactor speed at an interval of 400 to 500 revolutions per minute at a temperature of 20° to 40° C. is sufficient. The mixing process takes about sixty minutes. The consistency of the mixed mass may not be mealy or dusty but must be pliable. After the mixing and extraction processes the mass will be dried at a temperature of approximately 50° C. until it reaches a steady level of moisture, and after the drying process is completed, the mass will be degranulated.

After the degranulating process the bioregulator in poweder form will be portioned and packed by corresponding machinery, whereby a wide spectrum of possibilities exists as to volumetric or gravimetric measuring out.

There are two basic forms of carrying out the procedure which depend on the purpose of the bioregulator. In the first form, 100 kilos of the ground biomaterial, which is put together in the abovementioned weight proportions, are processed for an hour with the seeds, $d = 3 \times 1\beta^{-5}$cm in size, in the reactor-mixer in a gradual manner with n-Butanol, until the mass reaches a plastic consistency. The procedure will be carried out at a temperature of +20° C., whereby the speed of the mixer is 400 revolutions per minute.

After the extraction process the mass will be dried at a temperature T=50° C. until a constant level of moisture is reached, and afterwards the degranulation will be carried out.

The obtained bioregulator can be used for the treatment of seeds of agricultural crops, either in the dry method or the wet method in additional seed treatment, and can also be used as an additive to the protective substance or within the production process of mineral fertilizers and protective substances.

In the second procedural form, the same amount of basic material from the abovementioned plants is used, but in the size $D = 1 \times 10^{-5}$ cm. The previously measured out quantities are slowly processed in the mixer for an hour with n-Butanol at a temperature of 40° C. until they reach a plastic consistency. The speed of the mixer is 500 revolutions per minute.

After the extraction process is completed, the mass is dried at a temperature of 50° C. and then degranulated.

The bioregulator obtained in this manner is suitable for the foliar spraying of cultured young plants, as well as for the treatment of the soil before sowing or before planting, etc.

After the granulation process the finished material is packaged in units of 200, 1000 and 2000 grams for example, depending on the needs of the consumer, whereby consideration must be given to the fact that the basis for agricultural use on cultured crops is 200 grams per hectare.

Since the obtained bioregulator is not inclined to absorb moisture, the packaging must not be of any special kind. The pouring weight of the bioregulator is 1.52 1/kg. The packaged product will be stored in closed rooms under storage conditions which are normal for such products. Under the aforementioned packaging and storage conditions, the product is stable for approximately five years.

The bioregulator can be applied in the following ways:

(a) as a spray in a water solution to treat the soil before sowing or before
    planting, (b) as a bioregulator seed treatment in factories, using the dry or the wet
    method, or in combination with protective substances, (c) as a foliar spray in a water solution for treatment of young cultured
    plants, and (d) as a bioregulator to be included in the manufacture of mineral fertilizers
    and/or protective substances.

The spraying treatment of the soil is carried out in a water solution, whereby the solution is further diluted with water. This depends upon the type of spraying equipment required for one hectare (100–150 liters). The bioregulator solution is to be applied to the prepared soil before sowing or before planting, either by itself or together with a reduced amount of liquid fertilizers (a reduction of 20% to 30%).

For smaller areas of land, it is possible to mix the bioregulator (200 grams per hectare) with sand and treat the soil by hand.

Bioregulator seed treatment in factories can be carried out further in two ways: during the dry procedure a powdering with protective substances and during the wet procedure the treatment of the seeds with protective substances.

In the dry procedure the powdery bioregulator is first homogenized with a reduced amount of the protective substance (a reduction of 10% to 15%) required for the powdering of the amount of seeds needed for one hectare. This mixture of the bioregulator and the protective substance is then used in the dry powdering of the seeds.

In the wet procedure the bioregulator (200 grams per hectare) is dissolved in water (1–2 liters) under intensive stirring and is then mixed with a 10% to 15% reduced amount of the protective substance solution required for the number of seeds needed per hectare. Then the wet procedure for the further treatment of the seeds is continued in the normal manner with mixed solutions of the bioregulator and the protective substance.

When the bioregulator is to be applied to smaller plots of land, the treatment of the seeds which have already been processed with protective substances using the dry method, is carried out in a powder drum. This can also be accomplished by hand with the amount of seeds required for one hectare. This type of bioregulator use is characteristic when smaller amounts of seeds (less than 1000 seeds), for instance for vegetables, are required or whenever fewer seeds per hectare are used (for instance for certain field cultures such as corn, sugar beet, sunflower and similar cultures).

An exception to the use of the bioregulator as a seed treatment for smaller plots of land is the potato. In this case, a bioregulator solution is prepared for foliar spraying.

The leaf treatment of young cultured plant species can be carried out alone (200 grams per hectare) or in combination with the spraying of a 10% to 15% reduced amount of protective substances and/or a 20% to 30% reduced amount of mineral fertilizers during the 3–7 leaf phase or, at the latest, and the conclusion of the blossoming period.

Significant effects are achieved through the use of mineral fertilizers and/or protective substances to which bioregulators have been added during the production process. The result is a unified and synergistic effect of the mineral fertilizers and/or the protective substances on the one hand and of the bioregulators on the other.

The amounts of bioregulators (200 grams per hectare) that are included in mineral fertilizers or protective substances are reduced by 20% to 30% in mineral fertilizers, or 10% to 15% in protective substances, according to the quality of the soil and of the seed material. Therefore, a separate application of the bioregulator is superfluous.

The number of applications and the amount of bioregulator to be used depends mainly on the plant type to be treated. Normally the bioregulator is applied one to three times using amounts of approximately 200 to 600 grams per hectare.

I claim:

1. Bioregulator based on plant raw materials which comprises the following main components belonging to the family Caryophillaceae:
   (a) 20 to 30 weight % Herniaria
   (b) 8 to 14 weight % Buffonia
   (c) 10 to 16 weight % Spergula
   (d) 30 to 40 weight % Ortega
   (e) 5 to 7 weight % Arenaria
   (f) 6 to 8 weight % Sagina, and
   (g) 4 to 6 weight % Holesteum 2. Bioregulator according to claim 1, wherein said main components are present in the following proportions:
   (a) 24.3 weight % Herniaria
   (b) 10.6 weight % Buffonia
   (c) 12.8 weight % Spergula
   (d) 34.7 weight % Ortega
   (e) 5.6 weight % Arenaria
   (f) 6.5 weight % Sagina, and
   (g) 4.3 weight % Holesteum 3. A method for producing a bioregulator, which comprises selecting the following plant-raw-material-based main components belonging to the family Caryophillaceae:
   (a) 20 to 30 weight % Herniaria
   (b) 8 to 14 weight % Buffonia
   (c) 10 to 16 weight % Spergula
   (d) 30 to 40 weight % Oretega
   (e) 5 to 7 weight % Arenaria
   (f) 6 to 8 weight % Sagina, and
   (g) 4 to 6 weight % Holestum grinding said main components separately in a mill to granules having an average diameter of 0.5 to 100 μm, admixing the ground components, adding an extracting substance comprising n-butanol to convert the admixture into a mass having a plastic consistency, and then drying the mass.

4. A method according to claim 3, wherein the main components are ground to a granule size of 1 to 3 μm.

5. A method according to claim 3, wherein the extracting substance is gradually added to the mixture over a period of about 60 minutes and at a temperature of the mixture of between about 20° C. and about 40° C. the mixture being constantly stirred at about 400 to 500 revolutions per minute while the extracting substance is being added, after which the mass with plastic consistency is dried at a temperature of about 50° C. until a constant level of moisture is reached and thereafter degranulation is carried out followed by packing of the degranulated mass.

6. A method according to claim 3, wherein said main components are present in the following proportions:
   (a) 24.3 weight % Herniaria
   (b) 10.6 weight % Buffonia
   (c) 12.8 weight % Spergula
   (d) 34.7 weight % Ortega
   (e) 5.6 weight % Arenaria
   (f) 6.5 weight % Sagina, and
   (g) 4.3 weight % Holesteum 7. A method according to claim 6, wherein the the main components are ground to a granule size of 1 to 3 μm.

8. A method according to claim 6, wherein the extracting substance is gradually added to the mixture over a period of about 60 minutes and at a temperature of the mixture of between about 20° C. and about 40° C. the mixture being constantly stirred at about 400 to 500 revolutions per minute while the extracting substance is being added, after which the mass with plastic consistency is dried at a temperature of about 50° C. until a constant level of moisture is reached and thereafter degranulation is carried out followed by packing of the degranulated mass.

* * * * *

UNITED STATES PATENT AND TRADEMARK OFFICE
CERTIFICATE OF CORRECTION

PATENT NO. : 4,872,900

DATED : October 10th, 1989

INVENTOR(S) : Branco R. Gajic

It is certified that error appears in the above-identified patent and that said Letters Patent is hereby corrected as shown below:

Title page:

In the heading of the patent, under [73], the assignee's name and address should read -- Patentverwertungsgesellschaft bürgerlichen Rechts, Götz Dorndorf and Branco Gajić, Frankfurt am Main, Federal Republic of Germany --

Signed and Sealed this

Thirtieth Day of October, 1990

Attest:

HARRY F. MANBECK, JR.

Attesting Officer

Commissioner of Patents and Trademarks